US012582692B2

(12) United States Patent
    Schildkraut

(10) Patent No.: US 12,582,692 B2
(45) Date of Patent: Mar. 24, 2026

(54) METHODS AND KITS FOR REDUCING MICROPLASTICS LEVELS AND/OR REDUCING OR MINIMIZING MICROPLASTICS ACCUMULATION RATES IN SUBJECTS

(71) Applicant: HAZEL'S HOLISTIC, LLC, Great Neck, NY (US)

(72) Inventor: Harry P. Schildkraut, Great Neck, NY (US)

(73) Assignee: Hazel's Holistic, LLC, Great Neck, NY (US)

( * ) Notice: Subject to any disclaimer, the term of this patent is extended or adjusted under 35 U.S.C. 154(b) by 277 days.

(21) Appl. No.: 18/402,862

(22) Filed: Jan. 3, 2024

(65) Prior Publication Data

US 2025/0213640 A1     Jul. 3, 2025

(51) Int. Cl.
| | |
|---|---|
| *A61K 36/9066* | (2006.01) |
| *A61K 31/01* | (2006.01) |
| *A61K 31/202* | (2006.01) |
| *A61K 31/732* | (2006.01) |
| *A61K 33/26* | (2006.01) |
| *A61K 36/05* | (2006.01) |
| *A61K 36/31* | (2006.01) |
| *A61K 36/8962* | (2006.01) |
| *A61K 36/9068* | (2006.01) |

(52) U.S. Cl.
CPC .......... *A61K 36/9066* (2013.01); *A61K 31/01* (2013.01); *A61K 31/202* (2013.01); *A61K 31/732* (2013.01); *A61K 33/26* (2013.01); *A61K 36/05* (2013.01); *A61K 36/31* (2013.01); *A61K 36/8962* (2013.01); *A61K 36/9068* (2013.01)

(58) Field of Classification Search
None
See application file for complete search history.

(56) References Cited

U.S. PATENT DOCUMENTS

| | | |
|---|---|---|
| 2008/0305096 A1 | 12/2008 | Verdegem et al. |
| 2016/0303063 A1 | 10/2016 | Levy et al. |

FOREIGN PATENT DOCUMENTS

| | | |
|---|---|---|
| EP | 3345623 A1 | 7/2018 |
| WO | 2021214209 A1 | 10/2021 |

OTHER PUBLICATIONS

Sayed et al. Natrual Antioxidants can Improve Microplastics-Induced Male Reproductive Impairment in the African Catfish *(Clarias gariepinus)*, Frontiers in Envriormental Science, vol. 9, Article 811466, 2022, pp. 1-10.*
"Force Factor: Better Turmeric Tablets", retrieved from the internet on Feb. 19, 2025: <https://web.archive.org/web/20220525140102/https://forcefactor.com/products/better-turmeric-tablets>, May 25, 2022, pp. 1-6.
Sayed, et al., "Natural Antioxidants can Improve Microplastics-Induced Male Reproductive Impairment in the African Catfish *(Clarias gariepinus)*", Frontiers in Environmental Science, vol. 9, Article 811466, 2022, pp. 1-10.
PCT International Search Report & Written Opinion dated Feb. 26, 2025 for co-pending PCT International Application No. PCT/US2025/010093.
English translation of EP3345623 to PM—International Ag.

* cited by examiner

*Primary Examiner* — Danah Al-Awadi
(74) *Attorney, Agent, or Firm* — Saul Ewing LLP; Domingos J. Silva; Chihao Wang

(57) ABSTRACT

Described herein is a method for reducing microplastic levels or reducing or minimizing microplastic accumulation rates in a subject, such as a human. The method includes administering to the subject orally an effective amount of a composition including: an iron (II) compound; a soluble fiber; a fruit or vegetable phytochemical; a turmeric powder or extract; a ginger powder or extract; an omega 3 compound; an alga; and lycopene. Also described herein is a kit for carrying out the methods described herein.

15 Claims, No Drawings

METHODS AND KITS FOR REDUCING MICROPLASTICS LEVELS AND/OR REDUCING OR MINIMIZING MICROPLASTICS ACCUMULATION RATES IN SUBJECTS

BACKGROUND

Microplastics are a globally emerging contaminant in the environment. Microplastics present in the environment have found their ways into the human bodies. For example, Schwabl et al. found microplastics in human stool samples (Ann. Int. Med. 2019, 171, 453), Amato-Lourenco et al. detected the presence of airborne microplastics in human lung tissue (*J. Hazard Mater.* 2021, 416, 126124), and Leslie et al. identified plastic particle pollution in human blood (*Environ. Int.* 2022, 163, 107199).

Considering that the identification of microplastics in human bodies happened only recently, it is not surprising that conclusive studies that link microplastics in human bodies and human health directly have not been reported.

Studies using animal models, however, have demonstrated various adverse effects of microplastics in non-human mammals. For example, Lu et al. found that polystyrene microplastics induced gut microbiota dysbiosis and hepatic lipid metabolism disorder in mice (*Sci. Total Environ.* 2018, 631-632, 449-458); Deng et al. found that the issue accumulation of microplastics in mice is associated with widespread health risks, including disorders of energy and lipid metabolism (*Sci. Rep-Uk* 2017, 7, 46687); Jin et al. found that polystyrene microplastics induced male reproductive toxicity in mice (*J. Hazard Mater.* 2021, 401, 123430); Lim et al. observed decreased level of leukocyte and lymphocyte in the blood of Sprague-Dawley rats in response to polystyrene micro(nano)plastics inhalation (Chemosphere 2021, 262, 128330); Araujo et al. (*J. Hazard Mater.* 2021) noted decreased locomotor activity mice (which may be associated with a high anxiety and loss of risk assessment behavior) after consumption of polyethylene microplastics.

Furthermore, using primary human cells and human cell lines, researchers have found that microplastics have cytotoxicity. For example, Wang et al. (*Environ. Health Persp.* 2021, 129, 129) found that HK-2 cells (a proximal tubular cell derived from a normal, human adult male kidney) exposed to polystyrene microplastics had higher ER stress and markers of inflammation; and Shi et al. (*Environ. Sci-Nano* 2021, 8, 2660-2675) showed that polystyrene, especially those have been subjected to UV-induced photodegradation, reduced cell viability, and caused oxidative stress, membrane damage and mitochondrial dysfunction in A549 cells (a human lung cancer cell line of hypotriploid alveolar basal epithelial cell origin).

Accordingly, there is a need for methods and kits for reducing microplastics levels and/or reducing microplastics accumulation rates. The present invention addresses this need.

SUMMARY

In some aspects, the present invention is directed to the following non-limiting embodiments:

Embodiment 1: A method of reducing microplastics levels and/or reducing or minimizing microplastics accumulation rates in a subject, the method comprising administering to the subject orally an effective amount of a composition comprising: an iron (II) compound; a soluble fiber; a fruit or vegetable phytochemical; a turmeric powder or extract; a ginger powder or extract; an omega 3 compound; an alga; and lycopene.

Embodiment 2: The method of Embodiment 1, wherein the iron (II) compound comprises ferrous sulfate.

Embodiment 3: The method of any one of Embodiments 1-2, wherein the soluble fiber comprises a pectin, optionally apple pectin.

Embodiment 4: The method of any one of Embodiments 1-3, wherein at least one of the following applies: (a) the fruit or vegetable phytochemical comprises a garlic powder or extract, optionally a powder or extract from a bulb of *Allium sativum*; (b) the fruit or vegetable phytochemical comprises a *Brassica* powder or extract, optionally a powder or extract from a sprout of *Brassica oleracea;*

Embodiment 5: The method of any one of Embodiments 1-4, wherein the turmeric powder or extract comprises a powder or extract from a rhizome of *Curcuma longa.*

Embodiment 6: The method of any one of Embodiments 1-5, wherein the ginger powder or extract comprises a powder or extract of the root of *Zingiber officinale.*

Embodiment 7: The method of any one of Embodiments 1-6, wherein the omega 3 compound comprises an omega-3 fatty acid, optionally alpha-linolenic acid (ALA), eicosapentaenoic acid (EPA), or docosahexaenoic acid (DHA).

Embodiment 8: The method of any one of Embodiments 1-7, wherein the omega 3 compound is included in the composition as a fish oil.

Embodiment 9: The method of any one of Embodiments 1-8, wherein the alga comprises a *Chlorella* alga, optionally *Chlorella pyrenoidosa.*

Embodiment 10: The method of any one of Embodiments 1-9, wherein the composition comprises: ferrous sulfate; apple pectin; a powder or extract from a bulb of *Allium sativum*; a powder or extract from a sprout of *Brassica oleracea*; a powder or extract from a rhizome of *Curcuma longa*; a powder or extract of the root of *Zingiber officinale*; a fish oil comprising eicosapentaenoic acid (EPA), or docosahexaenoic acid (DHA); *Chlorella pyrenoidosa*; and lycopene.

Embodiment 11: The method of Embodiment 10, wherein the amount of the ferrous sulfate in the composition ranges from about 1% w/w to about 3% w/w; the amount of the apple pectin in the composition ranges from about 0.5% w/w to about 20% w/w; the amount of the powder or extract from a bulb of *Allium sativum* in the composition ranges from about 0.5% w/w to about 20% w/w; the amount of the powder or extract from a sprout of *Brassica oleracea* in the composition ranges from about 0.5% w/w to about 20% w/w; the amount of the powder or extract of the root of *Zingiber officinale* in the composition ranges from about 0.5% w/w to about 20% w/w; the amount of the ginger powder or extract in the composition ranges from about 0.5% w/w to about 20% w/w; the amount of the fish oil in the composition ranges from about 0.5% w/w to about 20% w/w; the amount of the *Chlorella pyrenoidosa* in the composition ranges from about 0.5% w/w to about 20% w/w; and/or the amount of the lycopene in the composition ranges from about 0.5% w/w to about 20% w/w.

Embodiment 12: The method of any one of Embodiments 1-11, wherein the composition further comprises activated carbon, a gelatin, a cellulose, magnesium stearate, and/or silica.

Embodiment 13: The method of any one of Embodiments 1-12, wherein the daily dosage of the composition ranges from about 1000 mg to about 5000 mg.

Embodiment 14: The method of any one of Embodiments 1-13, wherein the microplastics comprises a polyethylene (PE) microplastic, a polypropylene (PP) microplastic, a polystyrene (PS) microplastic, a polyamide (PA) microplastic, a polyester (PES) microplastic, and/or an acrylic (AC) microplastic.

Embodiment 15: The method of any one of Embodiments 1-14, wherein the subject is a human.

Embodiment 16: A kit, comprising a composition and an instruction manual, wherein the composition comprises: an iron (II) compound; a soluble fiber; a fruit or vegetable phytochemical; a turmeric powder or extract; a ginger powder or extract; an omega 3 compound; an alga; and lycopene, and the instruction manual instructs that the composition is to be administered orally to a subject in an effective amount to reduce microplastics levels and/or reduce or minimize microplastics accumulation rates in the subject.

Embodiment 17: The kit of Embodiment 16, wherein the iron (II) compound comprises ferrous sulfate.

Embodiment 18: The kit of any one of Embodiments 16-17, wherein the soluble fiber comprises a pectin, optionally apple pectin.

Embodiment 19: The kit of any one of Embodiments 16-18, wherein at least one of the following applies: (a) the fruit or vegetable phytochemical comprises a garlic powder or extract, optionally a powder or extract from a bulb of *Allium sativum*; (b) the fruit or vegetable phytochemical comprises a *Brassica* powder or extract, optionally a powder or extract from a sprout of *Brassica oleracea*; Embodiment 20: The kit of any one of Embodiments 16-19, wherein the turmeric powder or extract comprises a powder or extract from a rhizome of *Curcuma longa*.

Embodiment 21: The kit of any one of Embodiments 16-20, wherein the ginger powder or extract comprises a powder or extract of the root of *Zingiber officinale*.

Embodiment 22: The kit of any one of Embodiments 16-21, wherein the omega 3 compound comprises an omega-3 fatty acid, optionally alpha-linolenic acid (ALA), eicosapentaenoic acid (EPA), or docosahexaenoic acid (DHA).

Embodiment 23: The kit of any one of Embodiments 16-22, wherein the omega 3 compound is included in the composition as a fish oil.

Embodiment 24: The kit of any one of Embodiments 16-23, wherein the alga comprises a *Chlorella* alga, optionally *Chlorella pyrenoidosa*.

Embodiment 25: The kit of any one of Embodiments 16-24, wherein the composition comprises: ferrous sulfate; apple pectin; a powder or extract from a bulb of *Allium sativum*; a powder or extract from a sprout of *Brassica oleracea*; a powder or extract from a rhizome of *Curcuma longa*; a powder or extract of the root of *Zingiber officinale*; a fish oil comprising eicosapentaenoic acid (EPA), or docosahexaenoic acid (DHA); *Chlorella pyrenoidosa*; and lycopene.

Embodiment 26: The kit of Embodiment 25, wherein the amount of the ferrous sulfate in the composition ranges from about 1% w/w to about 3% w/w; the amount of the apple pectin in the composition ranges from about 0.5% w/w to about 20% w/w; the amount of the powder or extract from a bulb of *Allium sativum* in the composition ranges from about 0.5% w/w to about 20% w/w; the amount of the powder or extract from a sprout of *Brassica oleracea* in the composition ranges from about 0.5% w/w to about 20% w/w; the amount of the powder or extract of the root of *Zingiber officinale* in the composition ranges from about 0.5% w/w to about 20% w/w; the amount of the ginger powder or extract in the composition ranges from about 0.5% w/w to about 20% w/w; the amount of the fish oil in the composition ranges from about 0.5% w/w to about 20% w/w; the amount of the *Chlorella pyrenoidosa* in the composition ranges from about 0.5% w/w to about 20% w/w; and/or the amount of the lycopene in the composition ranges from about 0.5% w/w to about 20% w/w.

Embodiment 27: The kit of any one of Embodiments 16-26, wherein the composition further comprises activated carbon, a gelatin, a cellulose, magnesium stearate, or silica.

Embodiment 28: The kit of any one of Embodiments 16-27, wherein the instruction manual instructs that a daily dosage of the composition ranges from about 1000 mg to about 5000 mg.

Embodiment 29: The kit of any one of Embodiments 16-28, wherein the microplastics comprises a polyethylene (PE) microplastic, a polypropylene (PP) microplastic, a polystyrene (PS) microplastic, a polyamide (PA) microplastic, a polyester (PES) microplastic, and/or an acrylic (AC) microplastic.

Embodiment 30: The kit of any one of Embodiments 16-29, wherein the subject is a human.

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

The present invention proposes a composition that, when administered orally, is able to reduces the levels of microplastics in human bodies, or reduces the rate at which the microplastics is accumulated.

Accordingly, in some aspects, the present invention is directed to a method of reducing levels and/or accumulation rates of microplastics in a subject, such as a human subject.

In some aspects, the present invention is directed to a kit for reducing levels and/or accumulation rates of microplastics in a subject, such as a human subject.

Definitions

As used herein, each of the following terms has the meaning associated with it in this section. Unless defined otherwise, all technical and scientific terms used herein generally have the same meaning as commonly understood by one of ordinary skill in the art to which this disclosure belongs. Generally, the nomenclature used herein and the laboratory procedures in animal pharmacology, pharmaceutical science, and organic chemistry are those well-known and commonly employed in the art. It should be understood that the order of steps or order for performing certain actions is immaterial, so long as the present teachings remain operable. Any use of section headings is intended to aid reading of the document and is not to be interpreted as limiting; information that is relevant to a section heading may occur within or outside of that particular section. All publications, patents, and patent documents referred to in this document are incorporated by reference herein in their entirety, as though individually incorporated by reference.

In the application, where an element or component is said to be included in and/or selected from a list of recited elements or components, it should be understood that the element or component can be any one of the recited elements or components and can be selected from a group consisting of two or more of the recited elements or components.

In the methods described herein, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." "About" as used herein when referring to a measurable value such as an amount, a temporal duration, and the like, is meant to encompass variations of ±20% or ±10%, in certain embodiments ±5%, in certain embodiments ±1%, in certain embodiments ±0.1% from the specified value, as such variations are appropriate to perform the disclosed methods.

Methods

In some aspects, the present invention is directed to a method of reducing microplastics levels in a subject.

In some aspects, the present invention is directed to a method of reducing and/or minimizing microplastics accumulation rates in a subject.

In some embodiments, the term "microplastics" herein refers to plastic particles having a diameter or equivalent diameter of five millimeters or less, and include plastic particles having a diameter or equivalent diameter of one millimeter or less (which are sometimes referred to as "nanoplastics" in the art). In some embodiments, the term "microplastics" include all plastic particles that are small enough to enter and/or stay in the system of the subject (such as a human subject), and can be detected in, e.g., blood or fecal samples.

In some embodiments, the microplastic level refers to the levels of microplastics as measured in a blood sample or a fecal sample of the subject.

In some embodiments, the method includes administering to the subject an effective amount of a composition that reduces microplastics levels, and/or reduces or minimizes microplastics accumulation rates in the subject.

In some embodiments, the composition includes an iron (II) compound; a soluble fiber; a fruit or vegetable phytochemical; a turmeric powder or extract; a ginger powder or extract; an omega 3 compound; an alga; and lycopene.

The iron (II) compound is not particularly limited. One of ordinary skill in the art would understand that multiple iron (II) compounds can be used for medication or supplements. For example, ferrous fumarate, ferrous gluconate, ferrous succinate, ferrous sulfate, and etc. have been used for such purposes. In some embodiments, the iron (II) compound includes one or more compounds in this paragraph. In some embodiments, the iron (II) compound includes ferrous sulfate.

In some embodiments, the soluble fiber includes guar gum, gum Arabic, locust bean gum, pectin, oat fiber, beta glucan, *psyllium*, gum acacia, xanthane gum, innuline, fructo-oligosaccharides (FOS), carrageenan, and the like. In some embodiments, the soluble fiber includes a pectin, such as an apple pectin.

In some embodiments, the fruit or vegetable phytochemical include powder and/or extracts of acai, alfalfa, apple, artichoke, apricot, asparagus, avocado, barley grass, bilberry, beans, bittermelon, beet, blackberry, broccoli, black current, Brussels sprouts, blueberry, cabbage, cantaloupe, cassava, carrot, cherry, cauliflower, coconut, celery, coriander, cranberry, chlorella, gauvas, corn, grape, cucumber, garlic, grapefruit, horseradish, hops, kale, kava, kamut, kiwi, lima beans, lemon, oat grass, mangos, olive, orange, parsley, papaya, peach, peach, peas, pear, pepper, pineapple, potato, plum, pumpkin, pomegranate, rice, raspberries, spinach, strawberry, spirulina, tangerines, squash, tomato, sweet potatoes, wheat germ, wheat grass, white kidney beans, and the like.

In some embodiments, the fruit or vegetable phytochemical includes a garlic powder or extract. In some embodiments, the fruit or vegetable phytochemical includes a powder or extract from a bulb of *Allium sativum.*

In some embodiments, the fruit or vegetable phytochemical includes a *Brassica* powder or extract. In some embodiments, the fruit or vegetable phytochemical includes a powder or extract from a sprout of *Brassica oleracea;*

In some embodiments, the turmeric powder or extract comprises a powder or extract from a rhizome of *Curcuma longa.*

In some embodiments, the ginger powder or extract comprises a powder or extract of the root of *Zingiber officinale.*

In some embodiments, the omega 3 compound includes an omega-3 fatty acid. In some embodiments, the omega-3 fatty acid is a polyunsaturated fatty acid having a double bond three atoms away from the terminal methyl group in the chemical structure. In some embodiments, the omega-3 fatty acid includes alpha-linolenic acid (ALA), eicosapentaenoic acid (EPA), docosahexaenoic acid (DHA), and the like.

In some embodiments, the omega 3 compound is included as a fish oil, such as oils from herrings, sardines, mackerels, salmons, halibuts, tunas, swordfishes, tilefishes, pollocks, cods, catfishes, flounders, groupers, sharks, gemfishes, and the like.

In some embodiments, the alga includes a *Chlorella* alga or a spirulina. In some embodiments, the alga includes *Chlorella pyrenoidosa, Chlorella vulgaris, Chlorella sorokiniana*, and the like.

In some embodiments, the composition includes: ferrous sulfate; apple pectin; a powder or extract from a bulb of *Allium sativum*; a powder or extract from a sprout of *Brassica oleracea*; a powder or extract from a rhizome of *Curcuma longa*; a powder or extract of the root of *Zingiber officinale*; a fish oil comprising eicosapentaenoic acid (EPA), or docosahexaenoic acid (DHA); *Chlorella pyrenoidosa*; and lycopene.

In some embodiments, the amount of the ferrous sulfate in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the apple pectin in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the powder or extract from a bulb of *Allium sativum* in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the powder or extract from a sprout of *Brassica oleracea* in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the powder or extract of the root of *Zingiber officinale* in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the ginger powder or extract in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the fish oil in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the *Chlorella pyrenoidosa* in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the amount of the lycopene in the composition ranges from about 0.05% w/w to about 40% w/w, such as from about 0.1% w/w to about 35% w/w, from about 0.2% w/w to about 30% w/w, from about 0.3% w/w to about 25% w/w, from about 0.5% w/w to about 20%, or from about 1% w/w to about 3% w/w.

In some embodiments, the composition further includes charcoal, such as activated carbon.

In some embodiments, the composition further includes a gelatin, a cellulose, a magnesium stearate, or silica.

In some embodiments, a daily dosage of the composition ranges from about 500 mg to about 10000 mg, such as from about 1000 mg to about 5000 mg, from about 1500 mg to about 4000 mg, or from about 2000 mg to about 3500 mg.

In some embodiments, the microplastics comprises a polyethylene (PE) microplastic, a polypropylene (PP) microplastic, a polystyrene (PS) microplastic, a polyamide (PA) microplastic, a polyester (PES) microplastic, and/or an acrylic (AC) microplastic.

In some embodiments, the subject is a mammal. In some embodiments, the subject is a human.

Kit

In some aspects, the present invention is directed to a kit for reducing microplastics level in a subject.

In some aspects, the present invention is directed to a kit of reducing and/or minimizing microplastics accumulation rates in a subject.

In some embodiments, the kit includes a composition that, when administered orally to a subject in an effective amount, reduces microplastics levels, and/or reduces or minimizes microplastics accumulation rates in the subject.

In some embodiments, the composition is the same as or similar to those described elsewhere herein, such as in the "Method" section.

In some embodiments, the kit further includes an instruction manual. In some embodiments, the instruction manual instructs that the composition is to be administered according to the method herein.

Combination Therapies

In some embodiments, the method or composition herein is combined with a method or a composition that treats, ameliorates or prevents a condition associated with microplastics.

In some embodiments, the subject is further administered at least one additional agent that treats, ameliorates, and/or prevents a disease and/or disorder contemplated herein. In other embodiments, the compound and the at least one additional agent are co-administered to the subject. In yet other embodiments, the compound and the at least one additional agent are co-formulated.

For example, animal studies have shown that exposure to microplastics may lead to oxidative stress, inflammation, and cancer (Prata et al., *Sci Total Environ.* 2020 February 1:702:134455). Accordingly, in some embodiments, the method and/or kit herein is combined with a method, a compound or a kit for treating, ameliorating and/or preventing such disease or disorders.

The compounds contemplated within the disclosure are intended to be useful in combination with one or more additional compounds. These additional compounds may comprise compounds of the present disclosure and/or at least one additional agent for treating neurodegenerative conditions, and/or at least one additional agent that treats one or more diseases or disorders contemplated herein.

A synergistic effect may be calculated, for example, using suitable methods such as, for example, the Sigmoid-Emax equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Oral Administration

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as corn-starch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the disclosure may be in the form of tablets or capsules prepared by conventional means with pharmaceutically acceptable excipients such as binding agents (e.g., polyvinylpyrroli-done, hydroxypropylcellulose or hydroxypropylmethylcel-lulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable addi-tives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

The present disclosure also includes a multi-layer tablet comprising a layer providing for the delayed release of one or more compounds of the disclosure, and a further layer providing for the immediate release of another medication. Using a wax/pH-sensitive polymer mix, a gastric insoluble composition may be obtained in which the active ingredient is entrapped, ensuring its delayed release.

Dosing

The effective amount or dose of the composition of the present disclosure depends on the age, sex and weight of the patient, and the current medical condition of the patient. The skilled artisan is able to determine appropriate dosages depending on these and other factors.

A suitable dose of a compound of the present disclosure may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose admin-istered on Wednesday, a second subsequent 5 mg per day dose administered on Friday, and so on.

In the case wherein the patient's status does improve, upon the doctor's discretion the administration of the modu-lator of the disclosure is optionally given continuously; alternatively, the dose of drug being administered is tempo-rarily reduced or temporarily suspended for a certain length of time (i.e., a "drug holiday"). The length of the drug holiday optionally varies between 2 days and 1 year, includ-ing by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the patient's condition, to a level at which the improved disease is retained. In certain embodiments, patients require intermittent treatment on a long-term basis upon any recurrence of symptoms and/or infection.

Those skilled in the art recognizes, or is able to ascertain using no more than routine experimentation, numerous equivalents to the specific procedures, embodiments, claims, and examples described herein. Such equivalents were con-sidered to be within the scope of this disclosure and covered by the claims appended hereto. For example, it should be understood, that modifications in assay and/or reaction con-ditions, with art-recognized alternatives and using no more than routine experimentation, are within the scope of the present application.

It is to be understood that wherever values and ranges are provided herein, all values and ranges encompassed by these values and ranges, are meant to be encompassed within the scope of the present disclosure. Moreover, all values that fall within these ranges, as well as the upper or lower limits of a range of values, are also contemplated by the present application.

EXAMPLES

The instant specification further describes in detail by reference to the following experimental examples. These examples are provided for purposes of illustration only, and are not intended to be limiting unless so specified. Thus, the instant specification should in no way be construed as being limited to the following examples, but rather, should be construed to encompass any and all variations which become evident as a result of the teaching provided herein.

Example 1: Prophetic Example

Two compositions are prepared.

The first composition is the test composition. The first composition includes the test ingredients of ferrous sulfate, apple pectin, a powder prepared from the bulb of garlic *Allium sativum*, a powder prepared from the sprout of the broccoli *Brassica oleracea*, a powder prepared from the rhizome of turmeric *Curcuma longa*, a powder prepared from the root of ginger *Zingiber officinale*, a fish oil com-prising eicosapentaenoic acid (EPA), or docosahexaenoic acid (DHA); the alga *Chlorella pyrenoidosa*; and lycopene powder. The first composition further includes gelatin, microcrystalline cellulose, magnesium stearate, and silica.

The second composition is the control composition. The second composition also includes the same amount of gela-tin, microcrystalline cellulose, magnesium stearate, and silica, but does not include any of the test ingredients in the first composition. Rather, the second composition includes starch at an amount equal to the test ingredient in the first composition.

Same rodent subjects are separated into a test group and a control group. Both groups are administered with the same amount of microplastics (e.g., a polyethylene (PE) microplastic, a polypropylene (PP) microplastic, a polystyrene (PS) microplastic, a polyamide (PA) microplastic, a polyester (PES) microplastic, and/or an acrylic (AC) microplastic) orally. The test group is administered with 30 mg/kg per day of the first composition (test composition) orally, and the second test group is administered with 30 mg/kg per day of the second composition (control composition) orally. The amount of 30 mg/kg per day dosage translates roughly to a 2000 mg per day dosage in humans.

Before, during and after the administration of the first/ second composition, blood samples and fecal samples are collected from the two groups of rodent subjects.

The blood samples and fecal samples collected from the rodent subjects are analyzed for microplastic levels according to the time-of-flight secondary ion mass spectrometry method described in Jungnickel et al. (*Sci Total Environ.* 2016 September 1:563-564:261-6), the photoinduced forced microscopy method described in Leslie et al. (*Chem. Methods,* 1 (2021), pp. 205-209), as well as some other methods described in Ivleva (*Chem. Rev.* 2021, 121, 19, 11886-11936).

The microplastic levels from the two groups are compared. The results show that the blood/fecal microplastic levels before the administration of the first/second composition are comparable in the two rodent subject groups. For the samples collected during and after the administration of compositions, the microplastic levels are lower in the first group than in the second group.

The foregoing outlines features of several embodiments so that those skilled in the art may better understand the aspects of the present disclosure. Those skilled in the art should appreciate that they may readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions, and alterations herein without departing from the spirit and scope of the present disclosure.

What is claimed is:

1. A method of reducing microplastics levels, or reducing or minimizing microplastics accumulation rates, in a subject in need thereof, the method comprising administering to the subject orally an effective amount of a composition comprising: an iron (II) compound; a soluble fiber; a fruit or vegetable phytochemical; a turmeric powder or extract; a ginger powder or extract; an omega 3 compound; an alga; and lycopene.

2. The method of claim 1, wherein the iron (II) compound comprises ferrous sulfate.

3. The method of claim 1, wherein the soluble fiber comprises a pectin, optionally apple pectin.

4. The method of claim 1, wherein at least one of the following applies:

(a) the fruit or vegetable phytochemical comprises a garlic powder or extract, optionally a powder or extract from a bulb of *Allium sativum;*

(b) the fruit or vegetable phytochemical comprises a *Brassica* powder or extract, optionally a powder or extract from a sprout of *Brassica oleracea.*

5. The method of claim 1, wherein the turmeric powder or extract comprises a powder or extract from a rhizome of *Curcuma longa.*

6. The method of claim 1, wherein the ginger powder or extract comprises a powder or extract of the root of *Zingiber officinale.*

7. The method of claim 1, wherein the omega 3 compound comprises an omega-3 fatty acid, optionally alpha-linolenic acid (ALA), eicosapentaenoic acid (EPA), or docosahexaenoic acid (DHA).

8. The method of claim 1, wherein the omega 3 compound is included in the composition as a fish oil.

9. The method of claim 1, wherein the alga comprises a *Chlorella* alga, optionally *Chlorella pyrenoidosa.*

10. The method of claim 1, wherein the composition comprises:

ferrous sulfate;

apple pectin;

a powder or extract from a bulb of *Allium sativum;* a powder or extract from a sprout of *Brassica oleracea;* a powder or extract from a rhizome of *Curcuma longa;* a powder or extract of the root of *Zingiber officinale;* a fish oil comprising eicosapentaenoic acid (EPA), or docosahexaenoic acid (DHA);

*Chlorella pyrenoidosa;* and lycopene.

11. The method of claim 10, wherein the ferrous sulfate amount in the composition ranges from about 1% w/w to about 3% w/w;

the apple pectin amount in the composition ranges from about 0.5% w/w to about 20% w/w;

the amount of powder or extract from a bulb of *Allium sativum* in the composition ranges from about 0.5% w/w to about 20% w/w;

the amount of the powder or extract from a sprout of *Brassica oleracea* in the composition ranges from about 0.5% w/w to about 20% w/w;

the amount of the powder or extract of the root of *Zingiber officinale* in the composition ranges from about 0.5% w/w to about 20% w/w;

the amount of the ginger powder or extract in the composition ranges from about 0.5% w/w to about 20% w/w;

the fish oil amount in the composition ranges from about 0.5% w/w to about 20% w/w;

the *Chlorella pyrenoidosa* amount in the composition ranges from about 0.5% w/w to about 20% w/w; or the lycopene amount in the composition ranges from about 0.5% w/w to about 20% w/w.

12. The method of claim 1, wherein the composition further comprises activated carbon, a gelatin, a cellulose, magnesium stearate, or silica.

13. The method of claim 1, wherein he daily dosage of the composition ranges from about 1000 mg to about 5000 mg.

14. The method of claim 1, wherein the microplastics comprises a polyethylene (PE) microplastic, a polypropylene (PP) microplastic, a polystyrene (PS) microplastic, a polyamide (PA) microplastic, a polyester (PES) microplastic, or an acrylic (AC) microplastic.

15. The method of claim 1, wherein the subject is a human.

* * * * *